US00PP32678P3

(12) United States Plant Patent
Post

(10) Patent No.: US PP32,678 P3
(45) Date of Patent: Dec. 22, 2020

(54) ***CHRYSANTHEMUM* PLANT NAMED 'DLFSOLE2'**

(50) Latin Name: ***Chrysanthemum* X *morifolium***
Varietal Denomination: DLFSOLE2

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,325

(22) Filed: Mar. 19, 2020

(65) Prior Publication Data

US 2020/0305327 P1 Sep. 24, 2020

Related U.S. Application Data

(60) Provisional application No. 62/919,611, filed on Mar. 20, 2019.

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289
CPC ..... A01H 6/1424; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Chrysanthemum* plant named 'DLFSOLE2', characterized by its upright plant habit; vigorous growth habit; large dark green-colored leaves; uniform flowering habit; strong upright flowering stems typically grown as a single-stem (disbudded) cut flower; decorative-type inflorescences with bright yellow-colored ray florets; and relative resistance to *Fusarium oxysporum* f. sp. *chrysanthemi* and *Puccinia horiana* strain PhNL1.

2 Drawing Sheets

Figure 1:
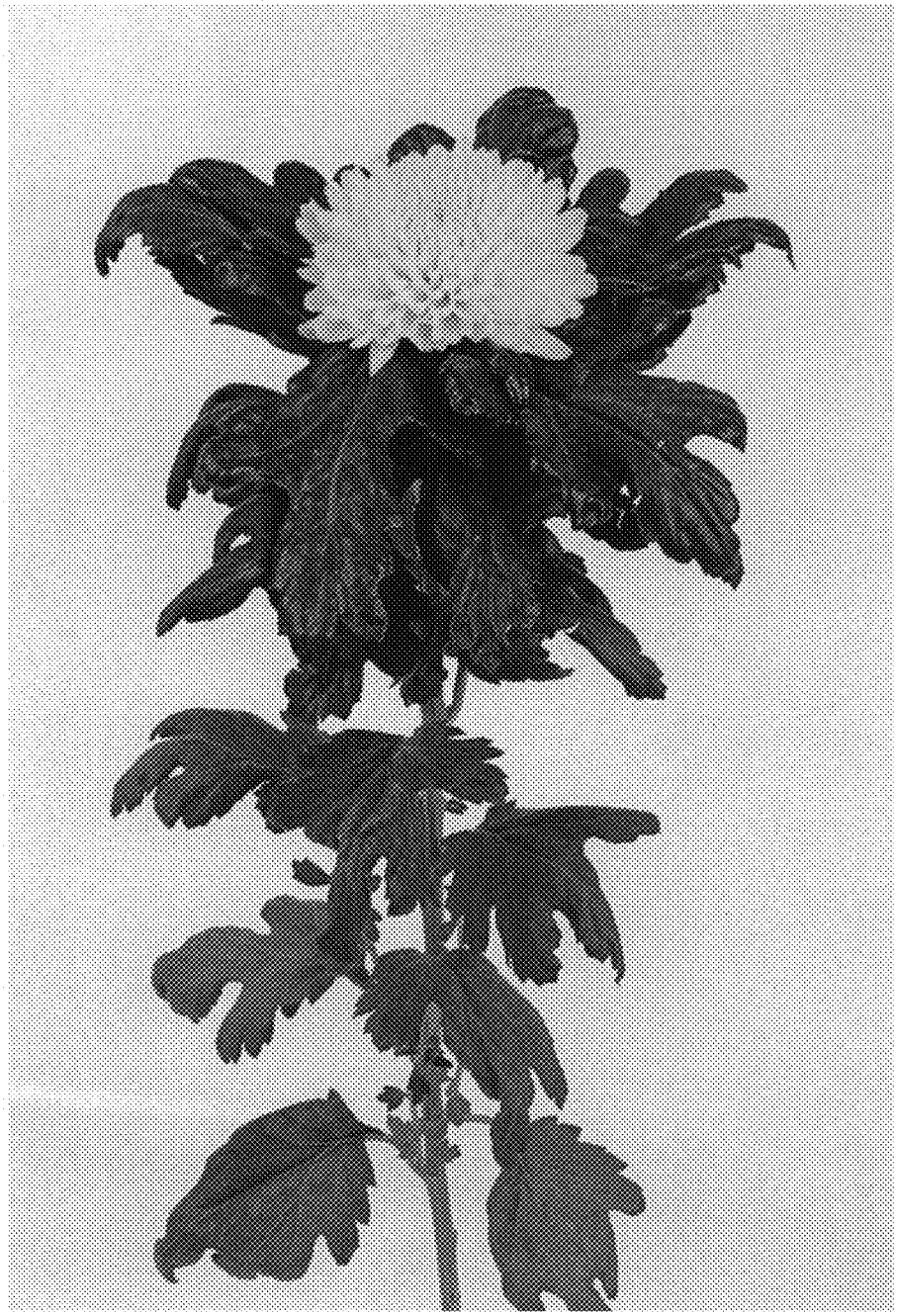

Botanical designation: *Chrysanthemum* X *morifolium*.
Cultivar denomination: 'DLFSOLE2'.

CROSS-REFERENCED TO CLOSELY-RELATED APPLICATIONS

Title: Varieties of *Chrysanthemum* Plants
Inventor/Applicant: Arie Gerard Post
Filed: Mar. 20, 2019
Ser. No.: 62/919,611
Inventor/Applicant hereby claim the benefit of this provisional U.S. Patent Application.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Aug. 24, 2018, application number A182425. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFSOLE2'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'Delisolemio', not patented. The new *Chrysanthemum* plant was discovered and selected as a single flowering plant from within a population of plants of 'Delisolemio' in a controlled greenhouse environment in Maasdijk, The Netherlands in September, 2015.

Asexual reproduction of the new *Chrysanthemum* plant by vegetative terminal cuttings since September, 2016 in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFSOLE2'. These characteristics in combination distinguish 'DLFSOLE2' as a new and distinct *Chrysanthemum* plant:

1. Upright plant habit; vigorous growth habit.
2. Large dark green-colored leaves.
3. Uniform flowering habit.
4. Strong upright flowering stems typically grown as a single-stem (disbudded) cut flower.
5. Decorative-type inflorescences with bright yellow-colored ray florets.
6. Relatively resistant to *Fusarium oxysporum* f. sp. *chrysanthemi* and *Puccinia horiana* strain PhNL1.

Plants of the new *Chrysanthemum* differ from plants of the mutation parent, 'Delisolemio', in ray floret color as plants of the new *Chrysanthemum* have bright yellow-colored ray florets whereas plants of 'Delisolemio' have greyed orange-colored ray florets.

Plants of the new *Chrysanthemum* can be compared to plants of *Chrysanthemum* X *morifolium* 'Zembla Yellow', disclosed in U.S. Plant Pat. No. 14,733. In side-by-side comparisons, plants of the new *Chrysanthemum* differ primarily from plants of 'Zembla Yellow' in ray floret color as ray florets of plants of the new *Chrysanthemum* are brighter yellow in color than ray florets of plants of 'Zembla Yellow'. In addition, ray florets of plants of the new *Chrysanthemum* are more incurved than ray florets of plants of 'Zembla Yellow'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. The photograph on the first sheet (FIG. 1 of 2) comprises a side perspective view of a typical flowering stem of 'DLFSOLE2' grown as a disbud-type cut flower.

Figure 2:
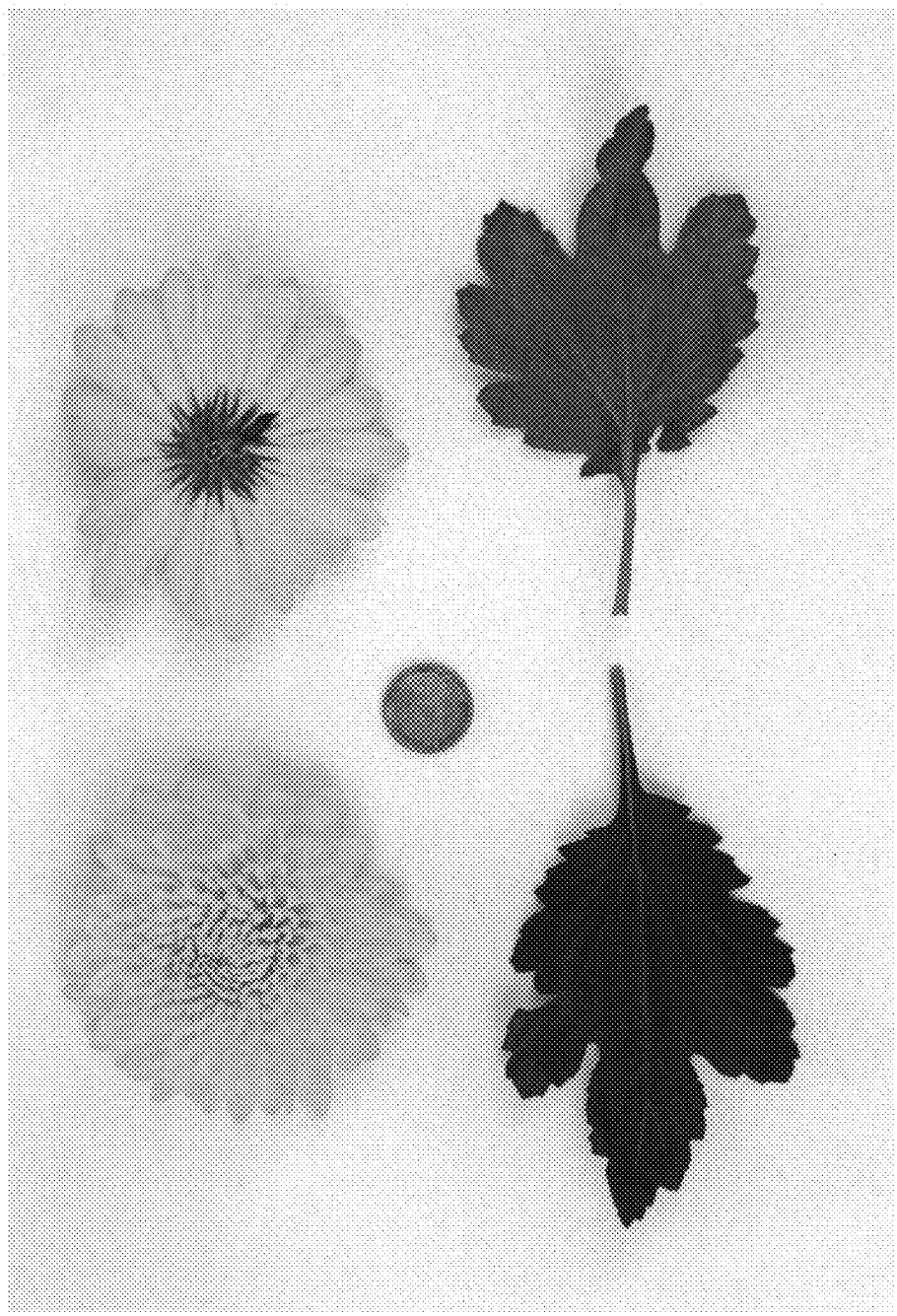

The photograph on the second sheet (FIG. 2 of 2) is a close-up view of lower (top of the photographic sheet) and upper (bottom of the photographic sheet) surfaces of typical inflorescences (left) and leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem disbud-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFSOLE2'.

Parentage: Naturally-occurring whole plant mutation of *Chrysanthemum* x *morifolium* 'Delisolemio', not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 72.4 cm.

*Plant height, soil level to top of inflorescence plane*.—About 75.8 cm.

*Plant diameter*.—About 26.5 cm.

*Flowering stem length*.—About 67.5 cm.

*Flowering stem diameter*.—About 7 mm.

*Flowering stem internode length*.—About 2.2 cm.

*Flowering stem strength*.—Strong.

*Flowering stem aspect*.—Erect.

*Flowering stem texture and luster*.—Densely pubescent; slightly glossy.

*Flowering stem color, developing*.—Close to 144A.

*Flowering stem color, developed*.—Close to 146A and 146C.

*Leaf description*.—Arrangement: Alternate; simple. Length: About 13 cm. Width: About 8.9 cm. Shape: Broadly ovate to broadly oblong. Apex: Short apiculate to acute. Base: Attenuate. Margin: Palmately lobed, coarsely crenate to serrate; sinuses convergent and moderately deep. Texture and luster, upper surface: Moderately pubescent, not rugose; moderately velvety; slightly glossy. Texture and luster, lower surface: Moderately pubescent, prominent venation; slightly velvety; very slightly glossy. Venation pattern: Pinnate, reticulate. Color: Developing leaves, upper surface: Close to 139A. Developing leaves, lower surface: Close to 147B. Fully developed leaves, upper surface: Slightly darker than between 139A and N189A; venation, close to 147B. Fully developed leaves, lower surface: Close to 147B; venation, close to 146B. Petioles: Length: About 2.4 cm. Diameter: About 2.5 mm by 3 mm. Strength: Moderately strong. Texture and luster, upper and lower surfaces: Moderately to densely pubescent; slightly glossy. Color, upper surface: Close to 146B; edges, close to NN137A. Color, lower surface: Close to 146B; edges, close to 137C. Stipules: Quantity and appearance: Two leafy stipules, opposite, at the petiole attachment to the stem. Length: About 6 mm. Width: About 5 mm. Shape: Broadly ovate. Texture and luster, upper surface: Moderately pubescent, not rugose; moderately velvety; slightly glossy. Texture and luster, lower surface: Moderately pubescent, prominent venation; slightly velvety; very slightly glossy. Color, upper surface: Slightly darker than between 139A and N189A. Color, lower surface: Close to 147B.

Inflorescence description:

*Appearance*.—Decorative uncurved inflorescence form with oblanceolate-shaped ray florets and tubular disc florets (disc florets are inconspicuous); inflorescences borne perpendicular to peduncles and face mostly upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 55 days later when grown as a disbud-type.

*Postproduction longevity*.—Good postproduction longevity; in an interior environment, inflorescences and foliage will maintain good color and substance for about two weeks; inflorescences persistent.

*Quantity of inflorescences*.—Grown as a disbud-type, all lateral inflorescences are physically removed and only the terminal inflorescence is allowed to develop; if grown as a spray-type, then typically about 18 inflorescences will develop.

*Inflorescence size*.—Diameter: Grown as a disbud type, about 10.4 cm and grown as a spray-type, about 7.6 cm. Depth (height): Grown as a disbud type, about 3.9 cm and grown as a spray-type, about 2.8 cm. Disc diameter: If present, about 5 mm.

*Receptacles*.—Height: About 4 mm. Diameter: About 9 mm. Shape: Flattened globular. Color: Close to 145C.

*Inflorescence buds*.—Height: About 1.8 cm. Diameter: About 1.5 cm. Shape: Broadly ovate to roughly globular. Texture and luster: Distally, smooth and glabrous; proximally, moderately pubescent; slightly glossy. Color: Close to 138A to 138C; immature ray florets, close to 3A and 1A.

*Ray florets*.—Quantity and arrangement: About 240 arranged in about eight whorls. Length: About 4.1 cm; varying between 2.3 cm and 5.1 cm. Width: About 1 cm; varying between 0.2 cm and 1.3 cm. Shape: Oblanceolate; moderately concave and moderately carinate. Apex: Bluntly and broadly acute to obtuse. Base: Attenuate. Margin: Entire; not undulate. Aspect: Initially upright to about 90° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 9A. When opening, lower surface: Close to 7B. Fully opened, upper surface: Close to 6A; venation, close to 6A; color does not change with development. Fully opened, lower surface: Close to 6B; venation, close to 6B; color does not change with development.

*Disc florets*.—Quantity and arrangement: If present, about one to four massed at the center of the receptacle; disc florets inconspicuous. Length: About 6 mm. Diameter: About 1 mm. Shape: Lower 85% fused into a tube; upper 15% free. Apex: Narrowly acute. Margin, distally: Entire. Texture and luster, inner and outer surfaces: Smooth, glabrous; glossy. Color, when opening, inner and outer surfaces: Close to 154D; towards the apex, close to 150A to 150B and towards the base, close to 145D. Color, fully opened, inner and outer surfaces: Close to 154D; towards the apex, close to 150A to 150B and towards the base, close to 145D.

*Involucral bracts*.—Quantity and arrangement: About 56 arranged in three whorls. Length: About 1.1 cm. Width: About 4 mm. Shape: Narrowly ovate to ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Close to 146B; margins, translucent and close to 196C to 196D and N199A. Color, lower surface: Close to 137C; margins, translucent and close to 196C to 196D and N199A.

*Peduncles*.—Length, terminal peduncle: About 3.9 cm. Diameter, terminal peduncle: About 4.5 mm. Length, third peduncle (when grown as a spray-type): About 8 cm. Diameter, third peduncle (when grown as a spray-type): About 3 mm. Strength: Strong. Aspect, terminal peduncle: Mostly upright. Aspect, third peduncle (when grown as a spray-type): About 35° from the flowering stem axis. Texture and luster: Densely pubescent; moderately glossy. Color: Close to 138A.

*Reproductive organs*.—Androecium: Present on disc florets only. Quantity: About five per floret. Filament length: About 1.5 mm. Filament color: Close to 145D. Anther size: About 0.5 mm by 3 mm. Anther shape: Narrowly oblong. Anther color: Close to 14A. Pollen amount: Moderate. Pollen color: Close to 17A. Gynoecium: Present on both ray and disc florets. Quantity: One per ray floret. Pistil length: About 4.5 mm. Style length: About 4 mm. Style color: Close to 150C. Stigma diameter: About 1 mm. Stigma shape: Cleft, decurrent. Stigma color: Close to 153C. Ovary color: Close to 145D.

*Seeds and fruits*.—To date, seed and fruit production have not been observed on plants of the new *Chrysanthemum*.

Pathogen & pest resistance: Plants of the new *Chrysanthemum* have been observed to be relatively resistant to *Fusarium oxysporum* f. sp. *chrysanthemi* and *Puccinia horiana* strain PhNL1. To date, plants of the new *Chrysanthemum* have not been observed to be resistant to pests and other pathogens common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFSOLE2' as illustrated and described.

* * * * *